United States Patent [19]

Cripe et al.

[11] Patent Number: 5,688,281

[45] Date of Patent: Nov. 18, 1997

[54] INTRAMEDULLARY ALIGNMENT GUIDE

[75] Inventors: Phil Cripe, Warsaw, Ind.; Cary M. Mauldin, Lake City, Fla.

[73] Assignee: Exactech, Inc., Gainesville, Fla.

[21] Appl. No.: 727,281

[22] Filed: Oct. 9, 1996

Related U.S. Application Data

[63] Continuation of Ser. No. 357,430, Dec. 16, 1994, abandoned.

[51] Int. Cl.$^6$ ................................................. A61B 17/56
[52] U.S. Cl. ............................................................ 606/88
[58] Field of Search ................................. 606/88, 87, 86, 606/89, 97, 99, 102, 80, 82, 79, 62, 63, 64, 72

[56] References Cited

U.S. PATENT DOCUMENTS

| | | | |
|---|---|---|---|
| 4,474,177 | 10/1984 | Whiteside. | |
| 4,487,203 | 12/1984 | Androphy | 606/88 |
| 5,417,694 | 5/1995 | Marik et al. | 606/88 |
| 5,445,642 | 8/1995 | McNuly et al. | 606/88 |

FOREIGN PATENT DOCUMENTS

| | | | |
|---|---|---|---|
| 340176 | 11/1989 | European Pat. Off. | 606/88 |
| 538153A | 4/1993 | European Pat. Off. | 606/88 |

OTHER PUBLICATIONS

Johnson and Johnson Orthopaedics brochure "P.F.C. Modular Knee System with Specialist Instruments" Dec. 1992, author unknown, pp. 1–13.

*Primary Examiner*—Guy V. Tucker
*Attorney, Agent, or Firm*—Fish & Richardson P.C.

[57] ABSTRACT

An intramedullary alignment guide and method for use thereof are disclosed for accurately preparing and shaping the distal femur end surface to receive a knee prosthesis for securement thereto. The guide references the femur intramedullary canal to ensure that a distal femoral resector is properly positioned at a selected angle with respect to a patient's mechanical axis. In the preferred embodiment, the intramedullary alignment guide includes an opening for inserting an intramedullary rod therethrough and into the intramedullary canal of a patient. The present guide includes an adjustment mechanism which allows a surgeon to quickly and easily deflect an attached distal femoral resector into a desired angular displacement with respect to intramedullary canal. In accordance with the preferred method, the distal femoral resector angled with respect to the intramedullary canal so that a cut can be made in a patient's distal femur end which is perpendicular with the patient's mechanical axis. The present guide can be used on patients having various anatomies, and in operations involving both the right and left legs. A sighting tool is also disclosed which allows a surgeon to externally verify that the distal femoral resector is properly aligned with the patient's mechanical axis.

16 Claims, 8 Drawing Sheets

INTRAMEDULLARY ALIGNMENT GUIDE

This is a continuation of application Ser. No. 08/357,430 filed Dec. 16, 1994, now abandoned.

BACKGROUND OF THE INVENTION

1. Field of the Invention

This invention relates to medical instruments and a method for use pertaining particularly to an improved intramedullary alignment guide for accurately preparing and shaping the distal femur end surface to receive a knee prosthesis to be secured thereto.

2. Description of Related Art

Knee surgery for the replacement and repair of knee joints has become commonplace in recent years. Total knee replacement systems and prostheses are available from a variety of manufacturers. Such total knee replacement systems, when properly installed, approximate the patient's natural knee movement. However, all knee prosthetic devices need to be properly fitted and installed to achieve an optimum fit and alignment. Proper alignment of the prosthetic device is critical to the successful outcome of a total knee replacement surgery. It is well known that it is desirable to provide an effective system of instruments and methods which ensure that the distal femur end is properly prepared for receiving the prosthetic device.

Some prior art systems have been developed which purport to assist a surgeon in preparing distal femur and proximal tibia ends for receiving knee prosthetic devices. One such system is shown in Petersen, U.S. Pat. No. 4,524,766. Petersen teaches a surgical knee alignment and cutting guide system which references a patient's mechanical axis, and from that reference, provides a cutting guide for shaping the patient's proximal tibia to receive the tibia portion of a knee prosthesis. Cutting guides are referenced from the tibia components of the knee prostheses for shaping the distal femur end to receive the femur portion of the knee prostheses. However, referencing from the patient's tibia introduces inaccuracies into the prosthetic alignment process. It is therefore desirable to provide an alignment system which references directly from the patient's distal femur end and provides for locating the patient's mechanical axis from the anatomic axis. By referencing from the patient's mechanical axis, an improved alignment system should employ an alignment guide and cutting guide to properly prepare the distal femur end for receiving the knee prosthetic device.

Another system for shaping the distal femur end is taught in Dunn, et al., U.S. Pat. No. 4,759,350. Dunn teaches a system of instruments for shaping the distal femur and proximal tibia surfaces to receive components of a knee prosthesis for knee replacement surgery. The Dunn system determines a patient's mechanical axis with reference to the patient's anatomic axis by using an alignment guide that is adapted to fit into a hole drilled into the distal femur end and intersecting the femoral intramedullary canal. Cutting guides or distal femoral resectors are attached to the alignment guide and are used to prepare the distal femur end to receive the femur portion of the prosthetic device.

The Dunn alignment guide is used to align the distal femoral resector or cutting guide so that a cut can be made in the distal femur end so as to provide a flattened bone end surface which is perpendicular to the patient's mechanical axis. The cut in the distal femur end is based upon a determination of the relative angular displacement of the patient's mechanical axis from the patient's anatomic axis.

To enable a surgeon to cut the distal femur end properly and at the appropriate angle with respect to the mechanical axis, the distal femoral cutting guide is displaced relative to the intramedullary alignment guide such that a cutting slot in the cutting guide is exactly perpendicular to the patient's mechanical axis. The distal femoral cutting guide is secured to the alignment guide using a plurality of pins. A surgeon can pivot the cutting guide such that a cutting slot in the cutting guide is exactly perpendicular to the patient's mechanical axis. A pivot pin is fitted into the distal femoral cutting guide to allow the guide to pivot slightly with respect to the intramedullary alignment guide. The surgeon uses an alignment pin which may be inserted through one of a plurality of holes in the distal femoral cutting guide to achieve the desired angular displacement between the cutting guide and the alignment guide.

Disadvantageously, the system taught by Dunn requires that the distal femoral cutting guide pivot about the medial condyle of the femur when a surgeon inserts an alignment pin through one of the plurality of holes in the cutting guide and into the alignment guide. By pivoting about the medial condyle of the femur, and not about the intramedullary canal, the Dunn system increases the length of the cut across the distal femur end as the angular displacement between the distal femoral cutting guide and the alignment guide is increased. Conversely, as the angular displacement between the cutting guide and the alignment guide is decreased, due to a small angular displacement between the patient's anatomic and mechanical axes, the length of the cut in the distal femur end is correspondingly decreased. Therefore, there is a need for an improved intramedullary alignment guide which provides proper angulation of the prepared distal femur end yet allows the distal femoral resector or cutting guide to be pivoted about the patient's intramedullary canal.

To ensure that proper limb alignment is restored to a patient, a combination of intramedullary alignment devices and extramedullary alignment check rods have been used. The combination of intramedullary alignment devices and extramedullary alignment check rods increase the probability for a successful clinical outcome.

The prior art systems for preparing distal femur ends for receiving knee prosthetic devices are difficult to assemble, require an inventory having a number of small, easily lost components, and require significant operating-room time for their use. For example, the system taught by Dunn includes a femoral alignment guide, an anterior femoral cutting guide with locator, a distal femoral cutting guide, an AP measuring guide, a femoral finishing guide, and a system for preparing the proximal tibia end. A surgeon, after opening the damaged knee area, sequentially uses these instruments to prepare a patient's distal femur and proximal tibia ends to receive knee components of a selected prosthetic device. The various components taught by Dunn are difficult to assemble, and have a number of components which may be lost or misplaced during use and storage. For example, the Dunn system requires use of a pivot pin, an alignment pin, and a plurality of additional pins which are used to secure the distal femoral cutting guide in place after alignment. These pins have proven difficult to use as they are small and numerous, and hence easily misplaced.

Therefore, there is a need for an improved intramedullary alignment guide which facilitates quick and accurate alignment guide rotation, has no loose parts, no loose pins, is easily assembled, and which therefore reduces the amount of operating-room time necessary to use. The present invention provides such an improved intramedullary alignment guide.

SUMMARY OF THE INVENTION

The present invention is an intramedullary (IM) alignment guide and method for use thereof which provides a means for aligning a distal femoral resector or cutting guide with the mechanical axis of a patient. Using the patient's intramedullary canal as a reference, the present IM guide provides a mechanism for ensuring that a surgeon positions a distal femoral resector perpendicular with the patient's mechanical axis. Using the present invention, a surgeon can quickly and easily align a distal femoral resector with the patient's mechanical axis by positioning the resector into a selected angle relative to the patient's anatomic axis. The present invention includes an adjustment mechanism which includes an adjustment rod, a rocker unit, and displacement pins. The adjustment rod includes a plurality of notches having inscriptions which correspond to the desired angular displacement of the distal femoral resector and the adjustment rod. By inserting an IM rod through the adjustment rod and into the patient's IM canal, and subsequently rotating the adjustment rod into a selected notch, the surgeon causes the displacement pins to deflect the distal femoral resector into a desired angular displacement with the adjustment rod. Thus, the surgeon can quickly and easily align the distal femoral resector so that a cut can be made in the patient's distal femur end which is perpendicular with the patient's mechanical axis.

The present IM guide accommodates various patient anatomies. The IM guide is relatively light and compact, easily assembled, and can be used to align cutting guides for both right and left knee surgeries. The present invention also includes an external alignment checking system having a quick attach/quick release sighting tool. The sighting tool includes a plurality of openings which allows the surgeon to verify whether the distal femoral resector is properly aligned with the patient's mechanical axis. If the resector is not properly aligned, the surgeon can easily realign the resector using the adjustment rod of the present invention. The realignment process is greatly simplified using the present invention because the surgeon does not need to disassemble and reassemble the alignment guide, nor does the surgeon need to remove the distal femoral cutting guide. Hence, the present invention reduces the overall operating room time and the costs related to knee surgery.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings refer to like elements.

DETAILED DESCRIPTION OF THE INVENTION

Throughout this description, the preferred embodiment and examples shown should be considered as exemplars, rather than as limitations on the present invention.

Patient Preparation and Anatomical Considerations

The present invention is preferably used to perform knee surgery on a patient, such as total knee replacement or arthroplasty. The success of a total knee replacement procedure is directly dependent upon re-establishing normal lower extremity alignment to the patient. To ensure that proper limb alignment is restored to the patient, the present invention provides an intramedullary guide that allows a surgeon to quickly and accurately align a distal femoral resector such that a cut can be made in the distal femur end which is perpendicular to the patient's mechanical axis.

Figure 1A:
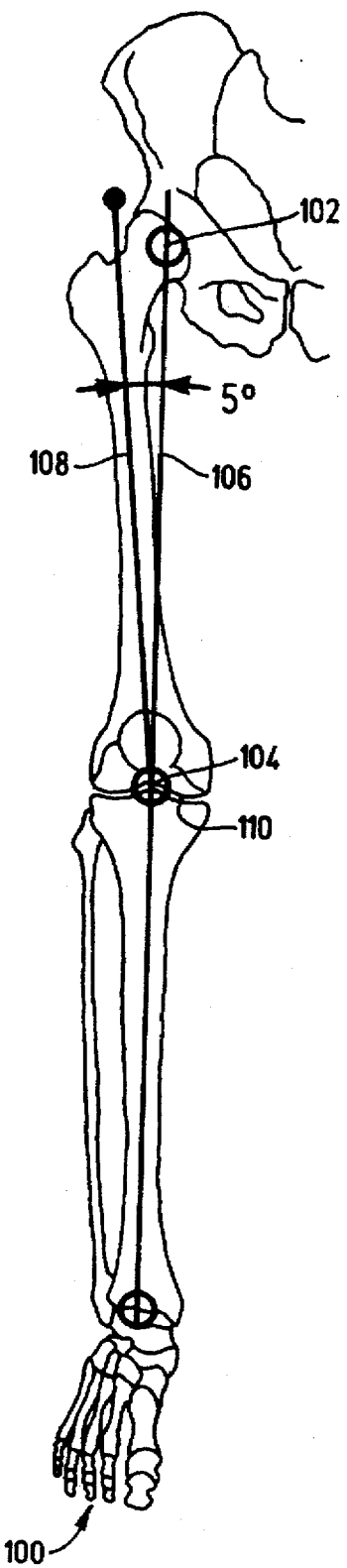
FIGS. 1A, 1B and 1C show the angular displacements between the mechanical and anatomic axes of three different human legs as determined from a developed radiograph of the three legs.
Figure 1B:
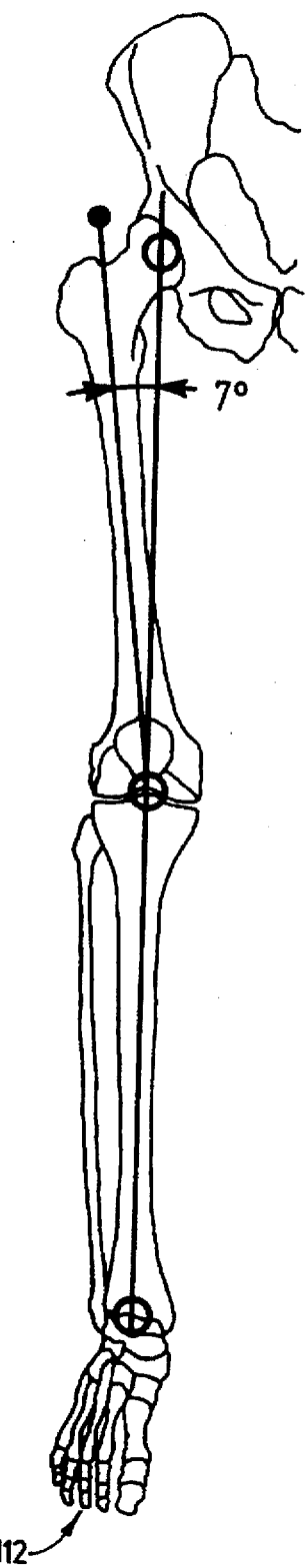
Figure 1C:
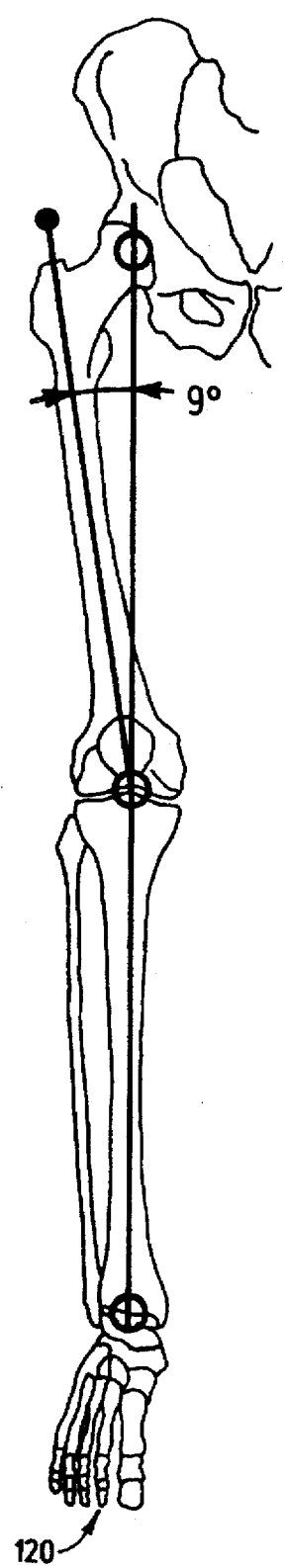

As is well known, a patient's mechanical axis is preferably established by drawing a line on an appropriate x-ray of a patient from the patient's hip, through the patient's knee, and to the patient's ankle when the patient is in a stable and erect position. FIG. 1 shows the femur and tibia bones of 3 different human legs 100, 112, and 120, wherein each leg has a different angular displacement between its respective mechanical and anatomic axes. As shown in FIG. 1, the mechanical and anatomic axes of each patient can be determined from a developed radiograph of a patient's leg. More specifically, the mechanical axis of the leg 100 is determined by drawing a line from the center of the femoral head 102 to the center of the distal femur at the knee 104. The mechanical axis of leg 100 is referred to in FIG. 1 by the line 106. The anatomic axis 108 of leg 100 is determined by drawing a line down the middle of the distal femoral shaft. As described in more detail below, an intramedullary alignment rod is typically fitted within the femoral shaft to coincide with and represent the anatomic axis. The angle between the two axes 106 and 108 is the angle that must be reproduced by the present invention during surgery so that a cut along the distal femur end 110 is perpendicular to the mechanical axis 106.

The angular difference between the mechanical and anatomic axes has been found in practice to typically be between about 5° and 6°. However, due to differences in patient anatomy, the angular displacement can range from about 3° to 9°. For example, the angular displacement between the anatomic and mechanical axes of the leg 100 is 5°. However, due to a broadened pelvis or significant coxa vara with long femoral necks, the legs 112 and 120 have angular displacements of 7° and 9°, respectively. The present invention advantageously provides a means for angulating a distal femoral resector by a range of angles relative to the anatomic axis which accommodates varied patient anatomies.

Once the angular difference between the patient's mechanical and anatomic axes are determined, a properly angled cut can be made in the distal femur end by referencing the patient's anatomic axis. The femoral canal, also known as the intramedullary canal, is used to reference the patient's anatomic axis. By using the intramedullary canal as a reference, and having a priori knowledge of the angular displacement between the anatomic and mechanical axes, the present invention provides an apparatus and method for aligning a distal femoral resector properly such that the distal femur end can be cut at an angle which is perpendicular to the mechanical axis of the patient. Therefore, once the anatomic axis is established, the amount of distal femur bone to be removed can be calculated, so that the resultant surface bone end forms a plane that is perpendicular to the mechanical axis.

Detailed Description of the Intramedullary Alignment Guide

Figure 2:
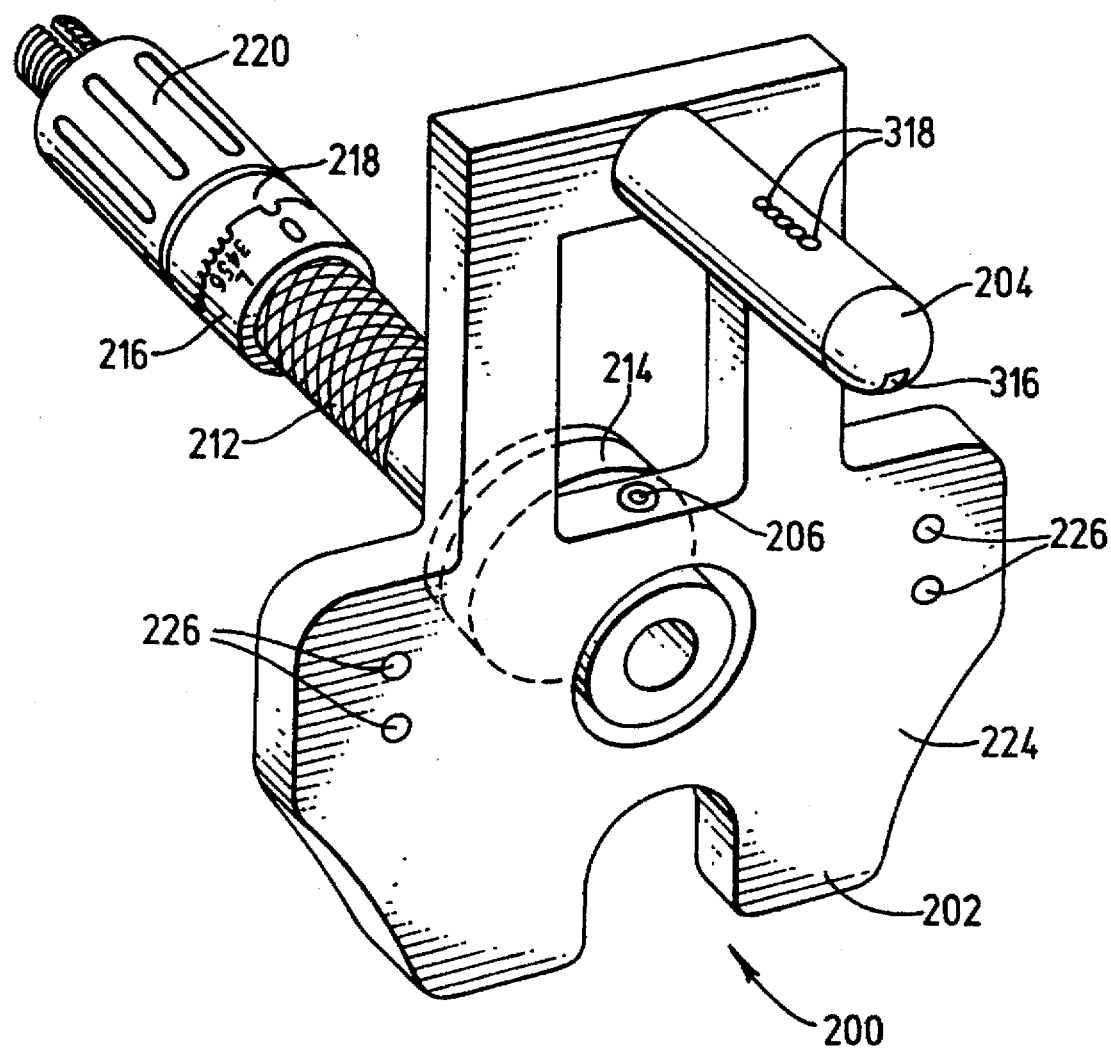
FIG. 2 shows a rear perspective view of the preferred embodiment of the present intramedullary (IM) alignment guide.
Figure 3:
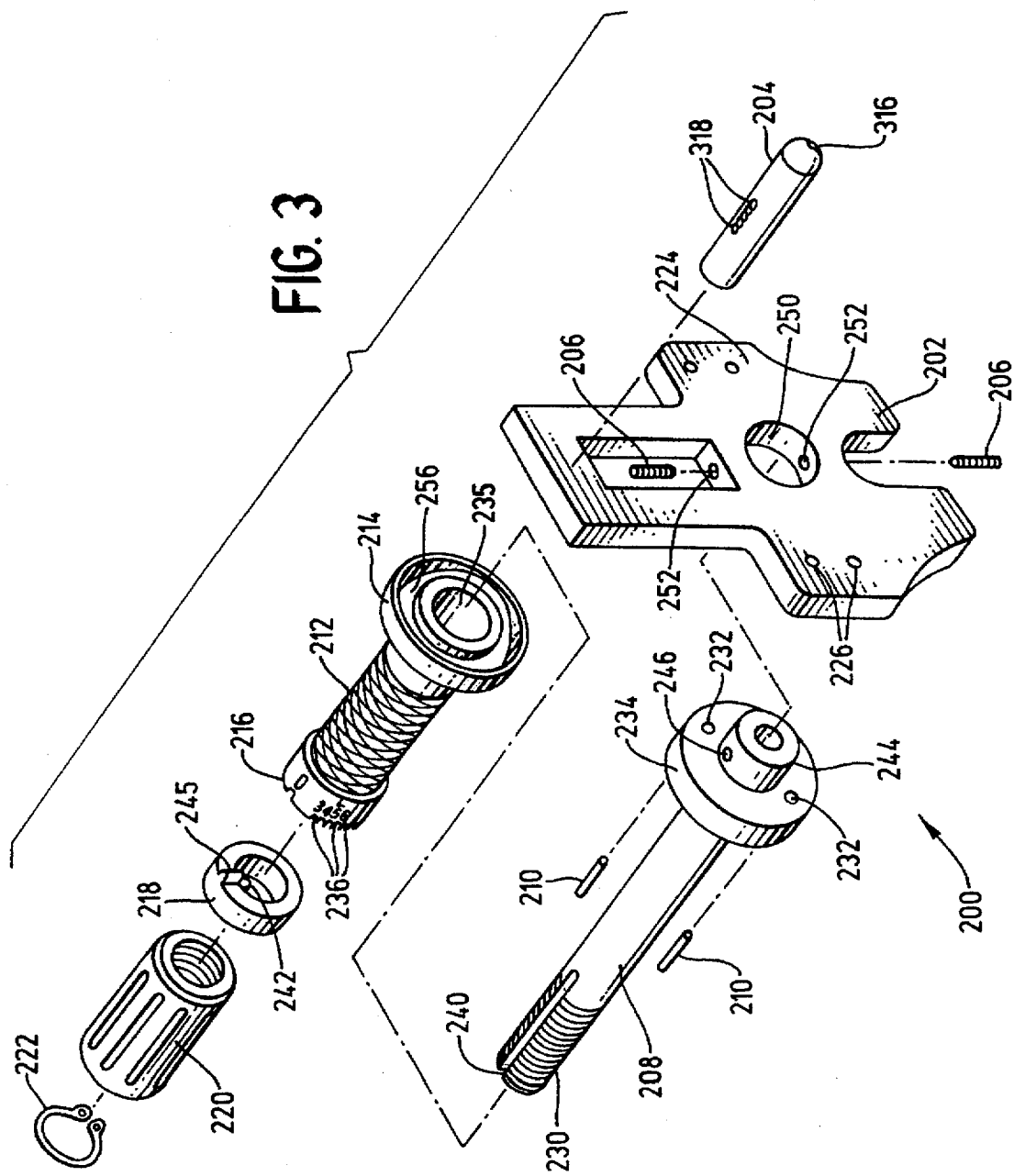
FIG. 3 shows an exploded view of the IM alignment guide of FIG. 2.

FIG. 2 shows a rear perspective view of the preferred embodiment 200 of the present intramedullary (IM) alignment guide. FIG. 3 shows an exploded view of the IM alignment guide of FIG. 2. Referring simultaneously to both FIGS. 2 and 3, the IM alignment guide 200 preferably comprises a base 202, a distal femoral resector attachment rod 204, a plurality of pivot pins 206, a cylindrical rocker unit 208, a plurality of displacement pins 210, an adjustment rod 212 having a base 214 and a top-facing interlock unit 216, an interlock ring 218, a locking knob 220, and a locking "C" ring 222. The IM alignment guide 200 preferably comprises surgical grade, bio-compatible materials, such as stainless steel, titanium, ceramic, structural plastics, etc. Preferably, the IM guide 200 is easily sterilized by known methods, such as heat sterilization, pressurized gas, and radiation sterilization methods. In the preferred embodiment, the base 202 is cut from a solid block of surgical grade stainless steel and is manufactured so that the top and bottom faces of the base 202 are substantially parallel to each other. The bottom face 224 of the base 202 preferably contains a plurality of holes 226 which are formed or drilled through to the top face of the base 202. The purpose of the holes 226 is described in more detail below with reference to the description of the use of the present invention during surgery.

The components which comprise the present invention are shaped to fit together as shown in FIGS. 2 and 3. As shown in FIG. 2, when assembled, the present IM alignment guide is a compact, easily manipulated unit. When assembled, the components are held in place by the C-ring 222 which is clamped around a threaded end 230 of the rocker unit 208. When assembled, the pins 210 are inserted through a plurality of holes 232 which are cut into a base section 234 of the rocker unit 208. The operation of the pins 210 and the base 234 is described in more detail below with reference to FIG. 4. As shown in FIG. 3, the adjustment rod 212 has a substantially hollow interior canal 235 which is shaped to receive the rocker unit 208. When assembled as shown in FIG. 2, the base 214 of the adjustment rod 212 abuts a top surface of the base section 234 of the rocker unit 208.

The interlock ring 218 has an inner diameter which is slightly greater than the outer diameter of the rocker unit 208 and the threaded end 230. During assembly of the IM guide 200, the interlock ring 218 is slipped over the threaded end 230 of the rocker unit 208 until it rests adjacent the top unit 216 of the adjustment rod 212. As shown in FIG. 3, the interlock ring 218 has a knob 245 which extends toward the top unit 216. The top unit 216 includes a plurality of notches 236 which are formed into a distal surface of the top unit 216. The notches 236 are spaced apart at precise locations on the distal surface of the top unit 216 so that when the knob 245 is placed into a selected one of the notches 236, the adjustment rod 212 rotates by a fixed degree of rotation. A detailed description of the operation of the guide 200, and more particularly the operation of the adjustment rod 212, the top unit 216, the interlock ring 218, and the notches 236, is given below with reference to FIGS. 4-6.

The locking knob 220 has a threaded interior channel which mates with the threaded end 230 of the rocker unit 208. Once the adjustment rod 212 and the interlock ring 218 are fitted over the rocker unit 208, the locking rod 220 is threaded onto the threaded end 230. The threaded end 230 includes a narrow slot 240 which extends from a distal end of the threaded end 230 and is formed lengthwise along the rocker unit 208. As shown in FIG. 3, the interlock ring 218 includes an inwardly-facing interlock knob 242 which is shaped to fit within the slot 240 of the rocker unit 208. Therefore, when the interlock ring 218 is slipped over the threaded end 230 of the rocker unit 208, the interlock knob 242 mates with the slot 240 and prevents the interlock ring 218 from rotating about the rocker unit 208. Once the locking knob 220 is threaded over the threaded end 230 of the rocker unit 208, the C-ring 222 is secured to a distal end of the threaded end 230. The C-ring 222 prevents the inadvertent disassembly of the IM alignment guide 200 during use. The C-ring 222 is preferably positioned on the threaded end 230 of the rocker unit 208 such that the locking knob 220 can be disengaged from the interlock ring 218 thereby allowing the adjustment rod 212 to be rotated into a desired position.

Referring again to FIG. 3, the base section 234 of the rocker unit 208 includes an extension 244 which has an outer diameter that is less than the outer diameter of the base section 234. The extension 244 of the base section 234 preferably includes two threaded holes 246 which are positioned at opposite sides of the extension 244. The threaded holes 246 are shaped to receive the pivot pins 206. The extension 244 of the base section 234 is inserted within a hole 250 formed through the base 202 of the alignment guide 200. During assembly, the extension 244 is inserted within the hole 250 and the pivot pins 206 are threaded through pivot holes 252 formed in the side walls of the hole 250 and into the holes 246 of the extension 244. When the rocker unit 208 is seated in the hole 250 by its extension 244, and the pivot pins 206 are threaded into the holes 246 of the extension 244, the rocker unit 208 pivots about the pivot pins 206.

The underside of the base 214 of the adjustment rod 212 includes an inclined annular groove 256. When the guide 200 is assembled as shown in FIG. 2, the adjustment rod 212 rotates about the rocker unit 208 and the inclined annular groove 256 rides upon distal ends of the displacement pins 210. Depending upon the degree of rotational displacement of the adjustment rod 212, the distal ends of the displacement pins 210 contact the inclined annular groove 256 at different locations along the groove. As described in more detail below with reference to FIG. 4, the points of contact between the distal ends of the displacement pins 210 and the inclined annular groove 256 determine the angular displacement of the base 202 with respect to the rocker unit 208. This angular displacement is used to properly align a distal femoral resector so that the patient's distal femur end can be cut at an angle which is perpendicular to the patient's mechanical axis.

Figure 4:
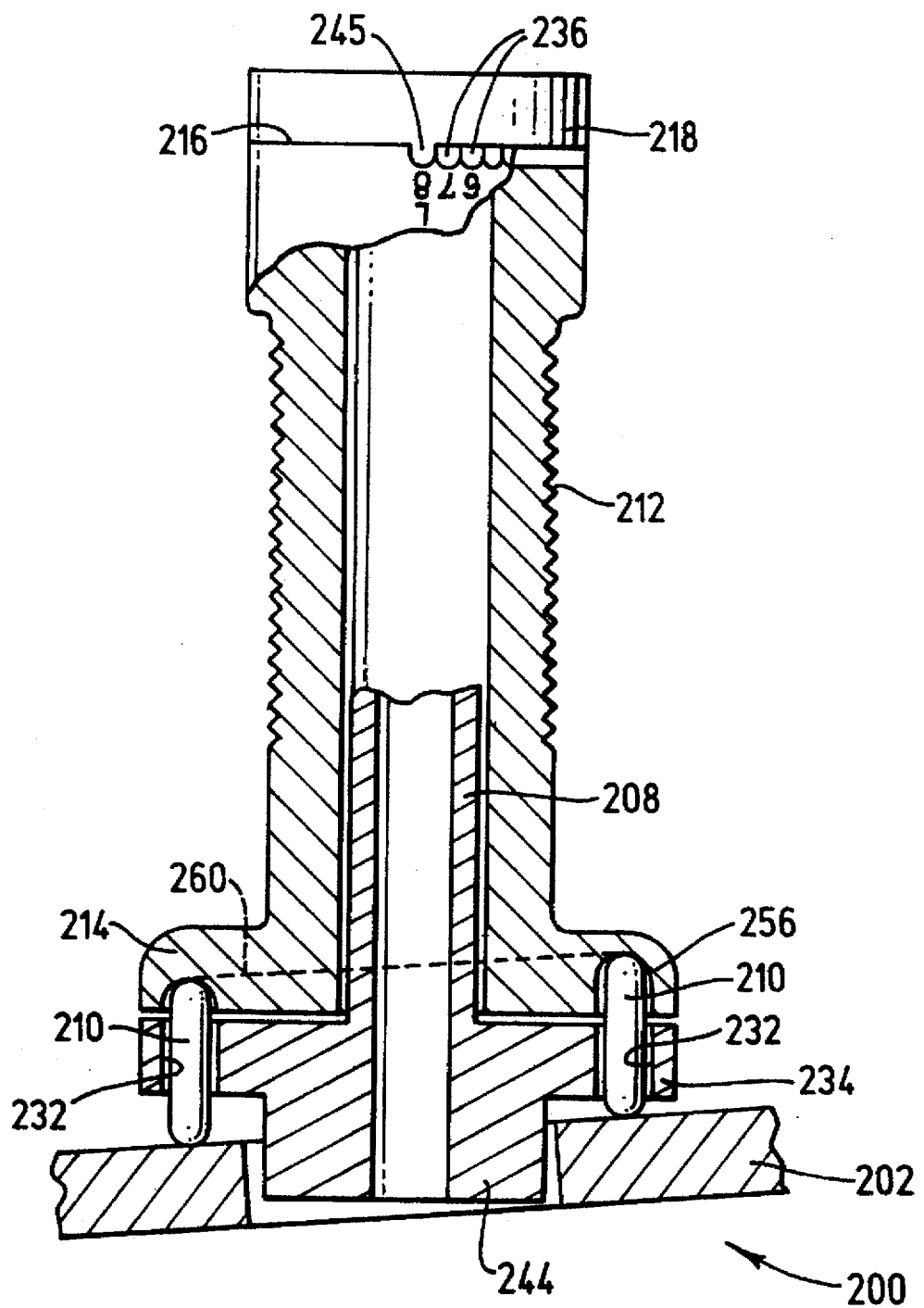
FIG. 4 shows a partial cut-away and cross-sectional view of the present invention showing details of the rocker unit, the displacement pins, and the base.

FIG. 4 shows a cross-sectional view of the present invention showing details of the rocker unit 208, the displacement pins 210, and the base 202. When the alignment guide 200 is assembled as shown in FIGS. 2 and 4, the displacement pins 210 are inserted through the holes 232 formed through the base section 234 of the rocker unit 208. One end of each displacement pin 210 abuts against a top surface of the base 202 of the alignment guide 200 as shown in FIG. 4. The other end of each displacement pin 210 fits within the inclined annular groove 256 formed in the underside of the base 214 of the adjustment rod 212. As shown in phantom in FIG. 4 via the dotted line 260, the inclined annular groove 256 varies in depth from one side of the base section 214 to the opposite side of the base section 214. More specifically, as shown in FIG. 4, the groove 256 is most shallow at the leftmost position of the base section 214. The groove 256 is deepest at the rightmost position of the base section 214. The angle that the base 202 makes with respect to the rocker unit 208 varies according to the rotational position of the adjustment rod 212 as it rotates about the rocker unit 208. Because the inclined annular groove 256 varies in depth along the diameter of the base 214, the displacement of the base 202 caused by the pins 210 varies according to the rotational position of the rod 212. The base 202 pivots with respect to the rocker unit 208 and rod 212 using the pivot pins 206 (FIG. 3). The base 202 is deflected at an angle with the rod 212 due to the degree of displacement produced by the displacement pins 210.

With the adjustment rod 212 first rotated into a starting neutral position, the displacement pins 210 contact the inclined annular groove 256 at contact points which are at equal depth within the base section 214. Therefore, at the starting neutral position, the rocker unit 208 and rod 212 are perpendicular to the base 202. As the adjustment rod 212 is rotated about the rocker unit 208, the displacement pins 210, due to the varying depth of the inclined annular groove 256, cause the base 202 to be deflected into various angles with respect to the rocker unit 208. For example, as shown in FIG. 4, the base 202 is deflected to a maximum angular displacement from the starting neutral perpendicular position. As the adjustment rod 212 is rotated, the positions at which the displacement pins 210 contact the inclined annular groove 256 change, and the amount of angular displacement of the base 202 with respect to the rocker unit 208 and rod 212 created by the displacement pins 210 changes accordingly. When the adjustment rod 212 is rotated into a position which causes the displacement pins 210 to produce an equal mount of linear displacement (i.e., when the points of contact of the displacement pins 210 with the inclined annular groove 256 are at equal depth), the base 202 is returned to a starting neutral angular position with respect to the rocker unit 208 (i.e., the base 202 is perpendicular to the rocker unit 208). As the adjustment rod 212 is rotated beyond the starting neutral position, the displacement pins 210 cause the base 202 to form an angle with the rocker unit 208 which is greater than 90°.

During use, the base 202 is placed into a desired angle with respect to the rocker unit 208 by manually adjusting the knob 212 and securing the knob 212 in the desired position by inserting the knob 245 of the interlock ring 218 into one of the notches 236 on the adjustment rod 212. The device is calibrated so that particular rotational positions of the adjustment knob 212 correspond to specific angular displacements. By selecting one of the rotational positions of the adjustment knob 212 and by inserting the knob 245 into one of the notches 236, the surgeon can quickly and easily change the angle that the base 202 makes with respect to the rocker unit 208. This angle corresponds to the measured angular displacement between the anatomic axis and mechanical axis, as described below in more detail with respect to FIGS. 5–7. As described below in more detail, the present invention accommodates angular displacements for both right and left legs.

Knee Surgery Using the IM Guide

As described above with reference to FIG. 1, once the angular difference between the patient's mechanical and anatomic axis is determined, the patient's femur channel or canal, also known as the intramedullary (IM) canal, is used to represent the patient's anatomic axis. A very accurate method of femoral component alignment is therefore provided by using the patient's IM canal as a reference. A pre-operative x-ray film is first taken to clearly show the canal on the x-ray. The x-ray is preferably a standing radiograph showing the center of the femoral head, the knee, and as much of the tibia as possible, preferably including the ankle. Alternatively, a single A/P radiograph of the entire femur will allow for correct calculation of the mechanical and anatomic axis. Once the anatomic and mechanical axes are established, the amount of distal femur removal may be calculated in a known fashion. The present IM alignment guide is used to ensure the surgeon that the distal femur end is cut at an angle which is perpendicular to the mechanical axis.

In practice, the patient's knee is prepared in a known manner to receive the components of a knee prosthesis. The femur and tibia ends are prepared independently, and either one can be prepared first. In practice, the distal femur end is routinely prepared first because the resection of the posterior femoral condyles offer greater exposure of the proximal tibia, thereby facilitating its preparation.

Figure 5:
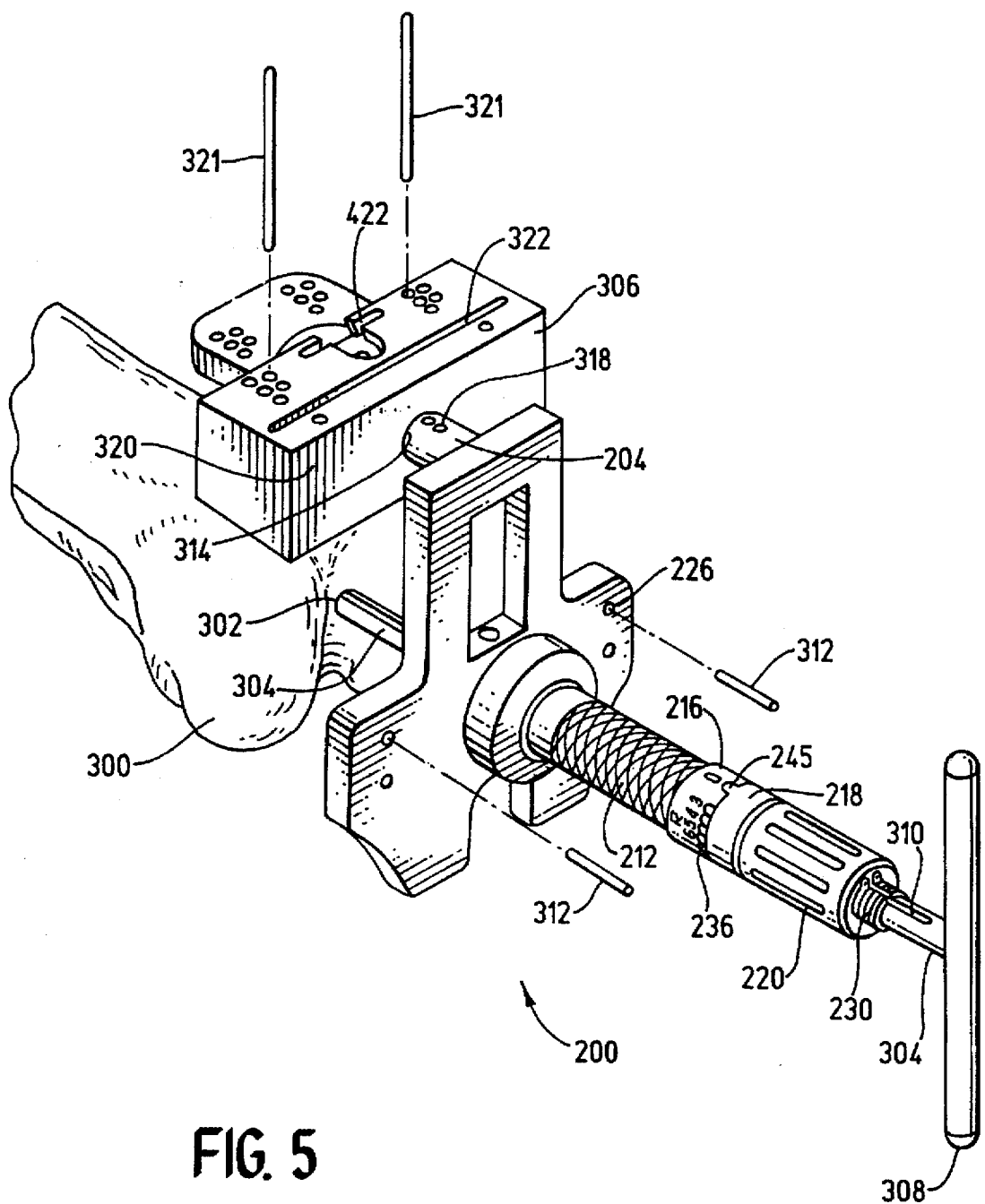
FIG. 5 shows the IM alignment guide of FIGS. 2–4 having an IM rod inserted through the IM guide and into the IM canal of a patient.

With the patient's knee opened appropriately and flexed, the site for inserting the intramedullary alignment guide of the present invention is selected on the distal femur, as shown in FIG. 5. The intramedullary canal of the femur is entered by drilling a hole 302 into the distal femur end. Care is exercised so that the drill avoids the patient's cortices. The hole drilled in the distal femur end is used for alignment in accordance with the present invention. Once the intramedullary canal is accessed, an intramedullary (IM) rod 304 is inserted therein. In practice, only the cancellous bone of the distal femur needs to be drilled, as the femur's hollow diaphysis usually provides no resistance to the insertion of the IM rod 304. The drilled hole 302 is necessary for alignment only and is not for component positioning on the distal femur. The alignment guide 200 is positioned on the distal femur with the bottom facing surface 224 of the base 202 of the alignment guide 200 facing the distal femur, as shown in FIG. 5. As described below in more detail, the alignment guide 200 is used in conjunction with the IM rod 304 to properly position a distal femoral resector or cutting guide 306 so that the surgeon can cut the distal femur end perpendicular to the mechanical axis. The IM guide 200 may optionally facilitate cutting the distal femur end at any desired angle with respect to the mechanical axis.

The T-shaped IM rod 304 includes a handle 308 and a plurality of flutes 310 cut along the length of the rod. The handle 308 of the IM rod allows a surgeon to easily manipulate the rod 304 during surgery. The flutes 310 serve two purposes: (1) they reduce air pressure which is potentially built up when the rod 304 is inserted within the IM canal, and (2) they serve as a channel for receiving the inwardly-facing interlock knob 242 described above with reference to the interlock ring 218. When the IM rod 304 is inserted within the IM guide 200, the interlock knob 242 is positioned within one of the plurality of flutes 310 which prevents the IM guide 200 from rotating with respect to the IM rod 304. Therefore, a surgeon can easily manipulate both the IM guide 200 and the rod 304 when the rod 304 is inserted through the guide 200.

The diameter of the rod 304 is preferably slightly smaller than the diameter of the drill bit which is used to form the hole 302 which accesses the patient's IM canal. The diameter of the rod 304 is preferably approximately 1 millimeter smaller than the diameter of the hole 302. There are two principal motivations for making the diameter of the rod 304 slightly less than the diameter of the hole 302. The first is to reduce the amount of pressure which is produced within the IM canal when the rod 304 is inserted therein. As is known, pressurization of the canal can lead to an increase of fat emboli in the blood stream, which can cause significant health problems. The second principal purpose for making the IM rod 304 with a smaller diameter than the hole 302 is to allow the IM rod to be principally guided by the patient's IM canal and therefore follow the patient's anatomic axis, and not be guided by the shape or orientation or position of the hole 302. By keeping the diameter of the rod 304 smaller than the diameter of the access hole 302, the IM rod 304 follows the patient's IM canal rather than the shape of the hole 302.

After the surgeon drills the hole 302 in the patient's distal femur end, the surgeon assembles the rod 304 into the IM guide 200 and places the assembled rod and guide over the distal femur end, as shown in FIG. 5. The rod 304 is inserted through the hole 302 and pushed into the patient's IM canal as shown. The rotation of the alignment guide 200 about the distal femur end is controlled by inserting a plurality of pins 312 through the plurality of holes 226 in the base 202 of the guide 200. The IM guide 200 can be secured to the distal femur end by inserting the pins 312 through the base 202 and into the patient's distal femur bone. A surgeon will typically know when the alignment guide 200 is correctly placed when an equal amount of medial and lateral femoral condyles are exposed posterior to the guide 200. When placing the guide 200 adjacent the patient's distal femur end, the surgeon should take into consideration the existence of bony anomalies.

Once the surgeon is satisfied with the placement of the IM guide 200 on the patient's distal femur end, a distal femoral cutting guide 306 can be attached thereto. As shown in FIG. 5, the distal femoral cutting guide 306 includes a receptacle 314 which is shaped to receive the distal femoral resector attachment rod 204 of the alignment guide 200.

The attachment rod 204 includes an insertion canal 316 (best shown in FIGS. 2 and 3) on the femur facing surface of the rod 204. The insertion canal is shaped to receive a small knob formed along the inner diameter of the receptacle 314 of the cutting guide 306. When the knobs in the inner diameter of the receptacle 314 is placed into the insertion canal 316 of the attachment rod 204, the guide 306 is inhibited from rotating around the rod 204. Therefore, once the guide 306 is placed over the rod 204, the guide 306 is locked into position by the rod 204.

The attachment rod includes a plurality of detents 318 (shown in FIGS. 2, 3, and 5) on a top-facing surface. As shown in FIG. 2, the attachment rod 204 preferably includes five detents 318 along its top-facing surface opposite the insertion canal 316. The detents 318 are preferably spaced apart at 1 millimeter increments. The detents 318 give a surgeon flexibility in positioning the distal femoral cutting guide 306 along the attachment rod 204. By aligning a front-facing surface 320 of the guide 306 with a selected detent 318, the surgeon can determine how far to displace the distal femoral cutting guide 306 from the base 202 of the alignment guide 200. The more that the surgeon displaces the cutting guide 306 from the base 202 of the alignment guide 200, the more bone the surgeon can remove from the patient's distal femur end. As shown in FIG. 5, the cutting guide 306 includes a perpendicular cutting slot 322 which is shaped to receive a cutting blade (not shown). During use, once the cutting guide 306 is properly positioned over the patient's distal femur end, the surgeon inserts the cutting blade through the perpendicular cutting slot 322 and removes bone from the patient's distal femur end. Alternatively, some surgeons dislike using a slotted cutting guide and prefer cutting along a flat surface. The present invention facilitates use of both a slotted and flat surface cutting guide, as shown in FIG. 5. The detents 318 in the attachment rod 204 allow a surgeon to displace the cutting guide 306 further along the patient's femur to a position which aligns the flat surface 320 of the guide 306 properly. The detents 318 allow a surgeon to displace the cutting guide 306 to a position where the surface 320 of the guide 306 can be used as a guide for the cutting blade rather than the slot 322. Thus, the present invention facilitates use of a cutting guide 306 by surgeons who prefer to use cutting slot guides similar to the cutting slot 322 and also by surgeons who prefer to use a flat surface cutting guide similar to the flat surface 320.

Figure 6:
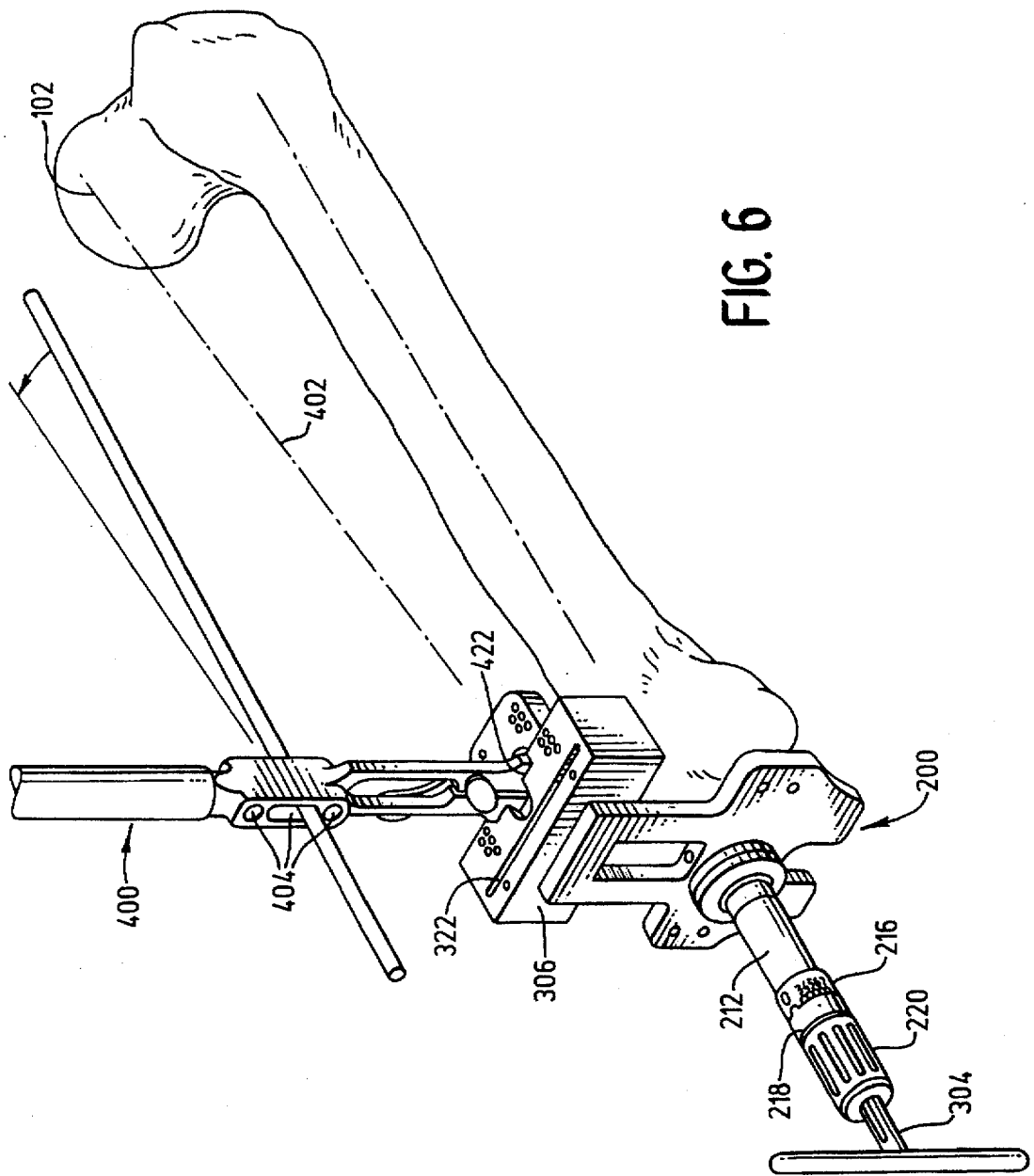
FIG. 6 shows a front perspective view of the IM guide of FIG. 5 having a quick attach/quick release sighting tool for externally verifying proper alignment of the guide with the patient's mechanical axis.

Once the cutting block 306 is placed over the attachment rod 204, the surgeon can properly align the cutting block 306 with the patient's mechanical axis. With the rod 304 inserted through the IM alignment guide 200 and the IM canal as shown in FIG. 5, the surgeon unlocks the interlock ring 218 from the top-facing interlock unit 216 of the adjustment rod 212 by rotating the locking knob 220 counterclockwise about the threaded end 230 of the rocker unit 208. After rotating the locking knob 220, the interlock ring 218, and more specifically the interlock knob 245, is disengaged from the top-facing unit 216 and the notch 236 into which the knob 245 was inserted. Once the interlock ring 218 is freed from the top-facing unit 216 of the adjustment rod 212, the surgeon can rotate the adjustment rod 212 so that the interlock knob 245 aligns with a desired one of the notches 236. As described above with reference to FIG. 4, the notches 236 are spaced apart in increments that determine the rotational displacement of the adjustment rod 212 about the rocker unit 208. Because the rotational displacement of the adjustment rod 212 with respect to the rocker unit 208 determines the points of contact of the displacement pins 210 with the inclined annular groove 256 (FIG. 4), the degree of rotational displacement of the adjustment rod 212 determines the angle that the base 202 makes with respect to the adjustment rod 212 and the rocker unit 208. In the preferred embodiment, the plurality of notches 236 in the top-facing unit 216 are spaced apart at intervals which correspond to 1° angular displacements of the base 202 with respect to the rod 212. As shown in FIGS. 4 and 5, the top-facing unit 216 preferably includes markings which correspond to the angular displacements that the base 202 makes with the rod 212 when the knob 245 is inserted within a selected notch 236 corresponding to that marking. For example, in the preferred embodiment, the notches 236 have corresponding labels three (3) to nine (9). Each number or marking represents the angle that the base 202 makes with respect to the adjustment rod 212 and the IM canal when the knob 245 is placed into a corresponding notch 236. There are notches 236 and corresponding markings on both sides of the neutral starting position notch 236. As shown in FIG. 5, the top-facing unit 216 is inscribed with markings for use of the present invention in a surgery on a right leg of a patient. FIG. 6 shows a different view of the top-facing trait 216 showing markings corresponding to notches 236 for use in surgery on a patient's left leg. Thus, the present invention can be used to align the cutting guide 306 with the mechanical axis for both a left and right leg. The surgeon simply rotates the adjustment rod 212 either clockwise (when operating on a right leg) from a top center position or counterclockwise (when operating on a left leg) from a top center position so that the knob 245 of the locking ring 218 is inserted into the notch 236 which corresponds to the previously determined angular difference between the patient's mechanical and anatomic axes.

For example, if the difference between the patient's mechanical and anatomic axes is 6°, and the surgeon is operating on the patient's right leg, with the IM guide 200, the IM rod 304 and the cutting block 306 assembled as shown in FIG. 5, the surgeon takes the following steps to align the cutting guide 306 with the patient's mechanical axis. The surgeon first releases the interlock ring 218 from the top-facing interlock unit 216 by rotating the locking knob 220 counterclockwise approximately one or two revolutions. The surgeon then rotates the adjustment rod 212 clockwise so that the locking knob 245 of the ring 218 is aligned with the notch 236 corresponding with the marking "R-6". The surgeon then rotates the locking knob 220 clockwise about the threaded end 230 until the locking ring 218 and knob 245 are fully inserted within the selected notch 236. Due to the operation of the displacement pins 210 as described above with reference to FIG. 4, the base 202 is forced into an angular displacement with the rod 212, rocker unit 208, and IM rod 304 exactly equal to 6°. Because the rod 304 is fully inserted within the IM canal of the patient, and because the IM canal corresponds to the patient's anatomic axis, the base 202 is therefore forced into an angle which is 6° with respect to the patient's anatomic axis. Because the attachment rod 204 is perpendicular to the base 202, the attachment rod 204, and thus the cutting guide 306, also makes a 6° angle with respect to the IM canal.

Accordingly, by simply rotating the adjustment rod 212 to align a desired notch 236 with the knob 245 of the interlock ring 218, the surgeon can quickly and easily align the cutting guide 306 with the patient's mechanical axis. If the surgeon determines that the alignment is inaccurate, realignment is quickly and easily accomplished using the present invention without the need to interchange parts or remove the rod. The IM guide 200, the IM rod 304, and the cutting guide 306 can all be left assembled as shown in FIG. 5 while the surgeon realigns the cutting guide 306. Therefore, operating-room time is decreased, which subsequently reduces the health risks to the patient and the costs associated with knee replacement surgery. To realign the cutting guide 306, the surgeon simply rotates the locking knob 220 counterclockwise one or two rotations to release the locking ring 218 from the rod 212. The rod 212 can thus be rotated to malign a new notch 236 with the knob 245. The process is repeated as described above until the surgeon is satisfied with the alignment. Once the surgeon determines that the cutting guide 306 is properly aligned, the cutting guide 306 can be secured to the patient's femur using securement pins 321.

Once the distal femoral cutting guide 306 is positioned and affixed to the patient's femur, the IM rod 304 and the IM guide 200 can be removed from the femur. Once the IM guide 200 and the IM rod 304 are removed, the distal femoral cutting guide 306 can be more securely affixed to the patient's femur using additional securement pins 321. Thereafter, the surgeon inserts a cutting blade through the cutting slot 322 formed through the distal femoral cutting guide 306. The saw blade (not shown) is then used appropriately to cut through the distal femur end in known fashion. This cut is perpendicular to the patient's mechanical axis and is made at a depth to the resection or cut in an amount of bone as will be replaced by the thickness of the femoral component of the knee prosthesis. Alternatively, the surgeon can cut through the distal femur end using the front-facing surface 320 of the cutting guide 306 as a guide. The cut surface must be flat to ensure a proper fit of the implant. The cut surface is then checked for flatness and, if necessary, is further shaped to ensure that the surface is completely flat and adequately positioned.

Referring now to FIG. 6, a quick attach/quick release sighting tool 400 is shown for use with the present alignment guide 200 and cutting guide 306. Once the surgeon properly aligns the cutting guide 306 with the patient's mechanical axis (shown in FIG. 6 as dotted line 402), the surgeon can externally verify proper alignment using the quick attach/quick release sighting tool 400. The sighting tool 400 has a plurality of openings 404 shaped to receive a sighting rod 406. With the guide 306 properly aligned as described above with reference to FIG. 5, the surgeon attaches the quick attach/quick release sighting tool 400 to the guide 306 as shown in FIG. 6 and as described in more detail below with reference to FIGS. 7a and 7b. When the sighting tool 400 is attached to the guide 306 as shown in FIG. 6, the openings 404 are parallel with the attachment rod 204 (FIG. 5) and therefore may be used to verify that the cutting slot 322 of the guide 306 is perpendicular to the patient's mechanical axis 402. To verify that the cutting slot 322 is perpendicular to the patient's mechanical axis 402, the surgeon inserts the sighting rod 406 through the openings 404. The surgeon then verifies that the sighting rod 406 aligns with the center of the patient's femoral head 102. If the sighting rod 406 properly aligns with the center of the femoral head 102, the surgeon removes the IM guide 200, the IM rod 304, the sighting rod 406 and the sighting tool 400 from the patient's knee. The surgeon then cuts the distal femur end as described above.

However, if the sighting rod 406 does not properly align with the center of the femoral head 102, the surgeon can quickly malign the cutting guide 306 by manipulating the locking knob 220 and the manual adjustment rod 212 appropriately as described above with reference to FIGS. 4 and 5.

Figure 7A:
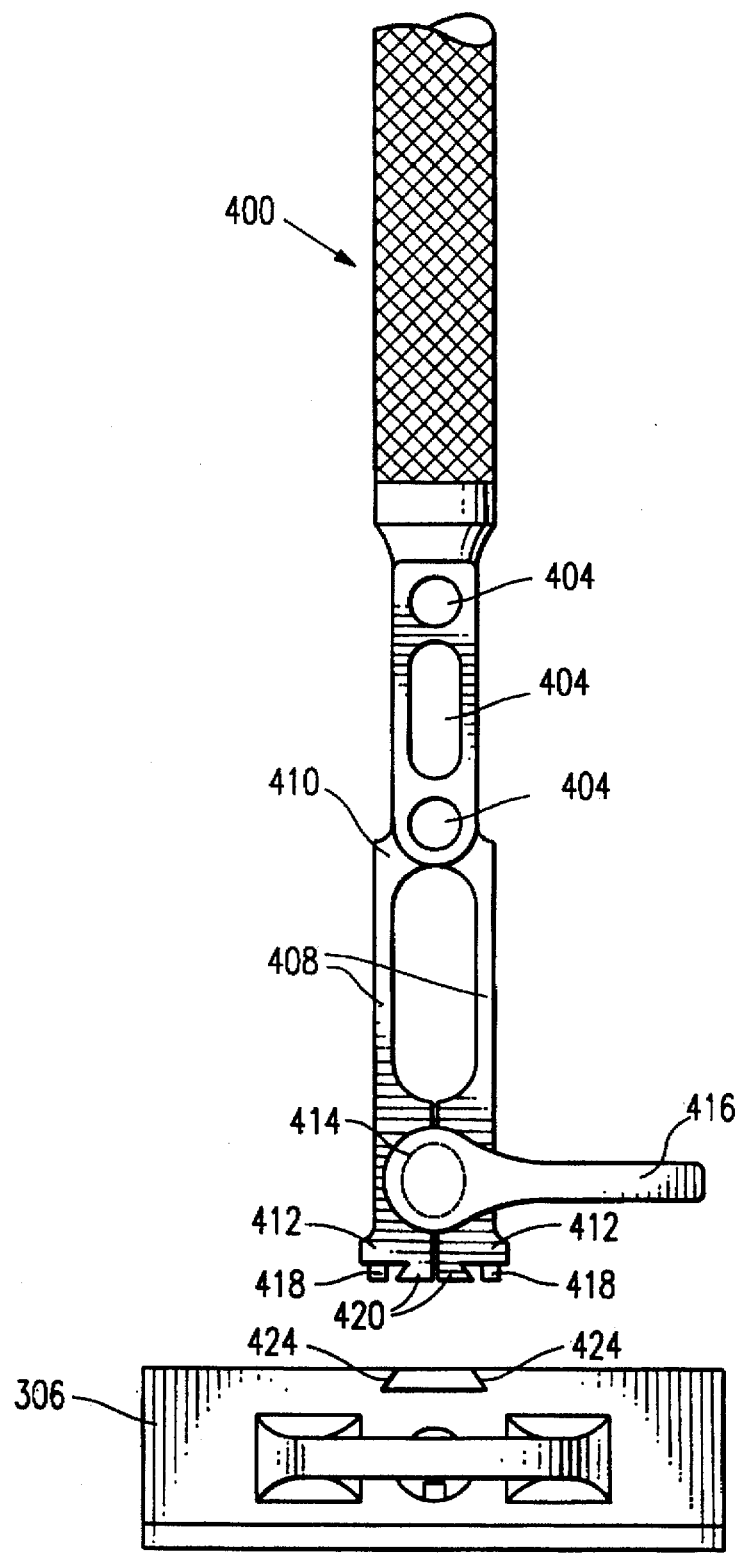
FIGS. 7a and 7b show details of the attach and release mechanism used to attach and release the sighting tool shown in FIG. 6 to a distal femoral resector.
Figure 7B:
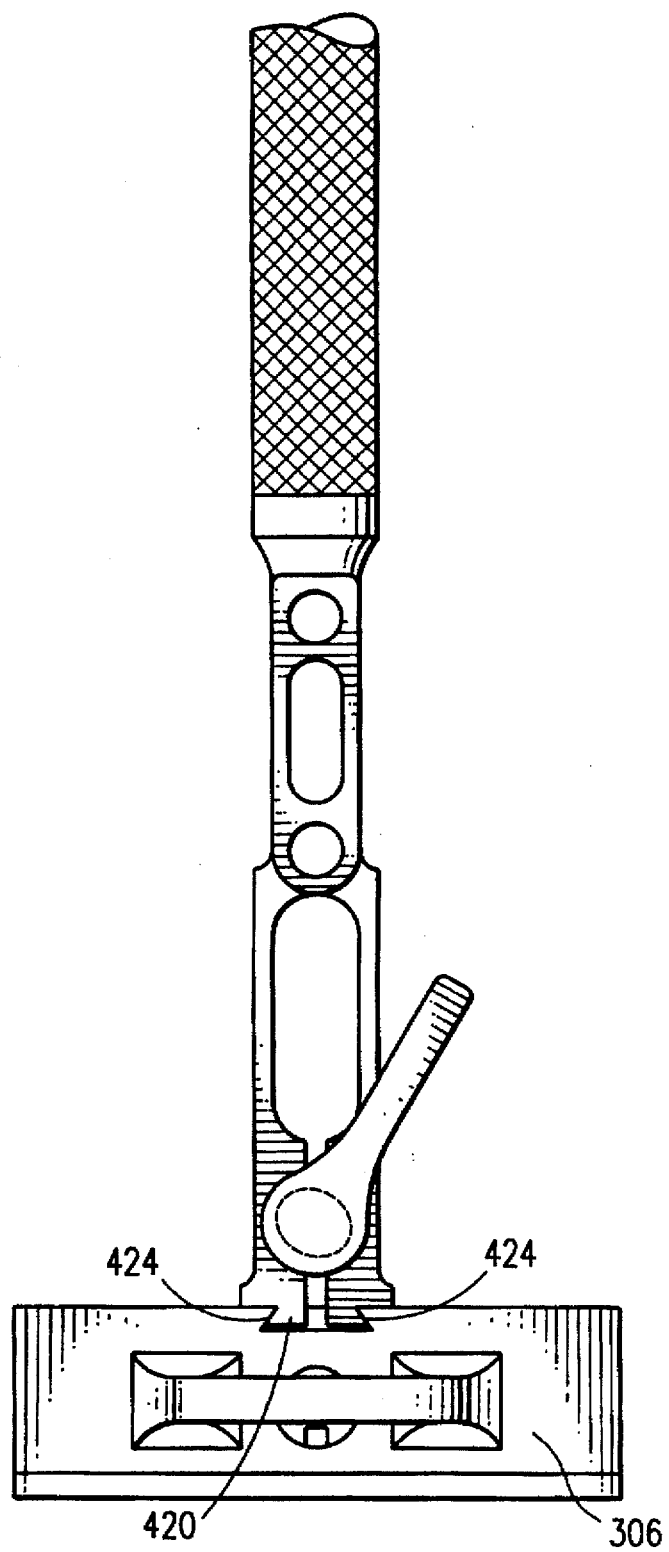

FIGS. 7a and 7b show details of the attach and release mechanism used to attach and release the sighting tool 400 to the distal femoral cutting guide 306. As shown in FIG. 7a, the sighting tool 400 is a cylindrical and substantially elongate tool which has a pair of juxtaposed mating tines 408 formed into a distal end of the sighting tool 400. The mating tines 408 are preferably formed from one solid piece 410 of the mating tool 400. As shown in FIG. 7a, when left undisturbed by an external force, mating ends 412 of the mating tines 408 are substantially proximate one another. However (shown in phantom in FIGS. 7a and 7b), the mating ends 412 can be forced apart in an elastic fashion by an elliptical cam 414 rotated between the mating ends 412 using a rotation lever 416. Because the cam 414 is elliptical, the ends 412 can be forced away from one another by rotating the lever 416 either clockwise or counterclockwise, as shown in FIG. 7b.

As shown in FIG. 7a, the mating ends 412 of the tines 408 include insertion knobs 418 and insertion dovetails 420. The insertion knobs 418 and dovetails 420 are used to interlock the sighting tool 400 with the cutting guide 306. As shown in FIGS. 5 and 6, the cutting guide 306 includes a sight rod slot 422 which is shaped to receive the insertion knobs 418. Thus, a surgeon can quickly attach the cutting guide 306 to the sighting tool 400 by inserting the insertion knobs 418 into the sight rod slot 422. The sight rod slot 422 guides the insertion knobs 418 as the surgeon rotates the elliptical cam 414 using the lever 416. As shown in FIG. 7b, with the insertion knobs 418 properly aligned within the slot 422 of the guide 306, the surgeon rotates the lever 416 so that the cam 414 pushes the tines 408 away from one another. The dovetails 420 are shaped to interlock with an interlock slot 424 formed into a top-facing surface of the cutting guide 306. Thus, as the surgeon rotates the lever 416, the sighting tool 400 mechanically interlocks with the cutting guide 306 due to the interlocking force (produced by the cam 414) of the dovetails 420 against the locking slots 424. The interlocking force maintained by the cam 414 is easily disengaged by rotating the lever so that the cam 414 is in a neutral position, as shown in FIG. 7a. Thus, the present invention provides a mechanism for facilitating the quick attachment and release of a sighting tool 400 from the cutting guide 306. The length of the sighting tool allows it to be used to assure rotational alignment of both the guide and other components which can be attached to the tool.

An improved intramedullary alignment guide and method for use thereof has been described. The present alignment guide provides a means for positioning a distal femoral cutting guide by a range of angles relative to the anatomic axis which accommodates various patient anatomies. Using the patient's intramedullary canal as a reference, the present IM guide provides a mechanism for ensuring that a distal femoral cutting guide is perpendicular with the patient's mechanical axis. The IM guide is easily assembled, can be used in knee surgeries on both right and left legs, and can be used to easily and quickly properly align the cutting guide with the patient's mechanical axis. An external alignment checking system using a quick attach/quick release sighting tool has also been described. The sighting tool is used with the present IM alignment guide to verify proper alignment of the cutting guide with the distal femur end.

A number of embodiments of the present invention have been described. Nevertheless, it will be understood that various modifications may be made without departing from the spirit and scope of the invention. Accordingly, it is to be understood that the invention is not to be limited by the specific illustrated embodiment, but only by the scope of the appended claims.

We claim:

1. A femoral alignment guide for positioning a distal femoral cutting guide at an angle which is perpendicular to a patient's mechanical axis, including:
   (a) a base having a plurality of securement holes formed therethrough for securing the base to a distal femur end of a patient, wherein the base includes an attachment rod shaped to receive a distal femoral cutting guide; and
   (b) an angular adjustment means having a longitudinal axis, pivotally and rotationally secured to the base, wherein rotation of the adjustment means pivots the base, and wherein rotation of the adjustment means about the axis deflects the base in accordance with the rotational position of the angular adjustment means to adjust the angle between the base and the axis.

2. The femoral alignment guide of claim 1, wherein the angular adjustment means comprises:
   (a) a substantially elongate rocker unit pivotally coupled to the base at a first end; and
   (b) a manual adjustment rod fitted over the rocker unit, wherein the rod has a first and a second end, and wherein the first end includes a plurality of spaced apart angular displacement positions, each position corresponds to a selected angular displacement of the base with respect to the adjustment rod, and wherein a user selects a desired angular displacement of the base with respect to the adjustment rod by rotating the adjustment rod about the rocker unit until a desired position is selected.

3. The femoral alignment guide of claim 1, wherein the attachment rod includes a plurality of spaced apart detents, wherein the detents correspond to distances for offsetting the distal femoral cutting guide from the base.

4. A femoral alignment guide for aligning a distal femoral cutting guide to a patient's mechanical axis, including:
   (a) a base having a plurality of securement holes formed therethrough for securing the base to a distal femur end of the patient, wherein the base includes an attachment rod shaped to receive a distal femoral cutting guide;
   (b) a substantially elongate rocker unit pivotally coupled to the base, the rocker unit having a first end;
   (c) an angular displacement means; and
   (d) a manual adjustment rod rotationally and coaxially fitted over the rocker unit, wherein the adjustment rod has a first and a second end, and wherein the first end includes a plurality of circumferentially spaced apart angular displacement notches and the second end engages the angular displacement means so as to deflect the rocker unit and coaxial adjustment rod with respect to the base upon rotation of the adjustment rod, wherein the rotational position of each notch corresponds to a selected angular displacement of the base with respect to the adjustment rod, and wherein a user selects a desired angular displacement of the base with respect to the adjustment rod by rotating the adjustment rod about the rocker unit until a desired notch is engaged.

5. The femoral alignment guide of claim 4, further including:
   (a) an angular displacement means, positioned at the second end of the adjustment rod, wherein the angular displacement means deflects the base into the desired angular displacement with respect to the adjustment rod.

6. The femoral alignment guide of claim 4, wherein the angular displacement means comprises an annular groove and a plurality of displacement pins inserted therein, and wherein the annular groove has a depth which varies with the rotational displacement of the adjustment rod about the rocker unit, and wherein the displacement pins deflect the rocker unit into the desired angular displacement with respect to the base.

7. The femoral alignment guide of claim 4, wherein the base is substantially flat, and wherein the base has a hole drilled therethrough for receiving the first end of the rocker unit.

8. The femoral alignment guide of claim 7, further including pivot pins mounted through the hole in the base and the first end of the rocker unit, wherein the rocker unit pivots about the pivot pins.

9. The femoral alignment guide of claim 4, wherein the rocker unit and the adjustment rod are substantially hollow.

10. The femoral alignment guide of claim 9, further including:
   (a) an intramedullary rod, inserted through the rocker unit, the adjustment rod and the base, wherein the intramedullary rod is configured to be inserted into a patient's intramedullary canal, wherein the intramedullary rod aligns the adjustment rod with the intramedullary canal, and wherein the selected angular displacement of the base with respect to the adjustment rod is substantially equal to an angle that the patient's mechanical axis makes with respect to the intramedullary canal.

11. The femoral alignment guide of claim 10, further including:

(a) an alignment verification means, coupled to the cutting guide, for verifying that the selected angular displacement of the base with respect to the adjustment rod is substantially equal to the angle that the patient's mechanical axis makes with respect to the intramedullary canal.

12. The femoral alignment guide of claim 11, wherein the alignment verification means comprises a substantially elongate sighting tool and a sighting rod, and wherein the sighting tool includes a plurality of sighting holes for inserting the sighting rod therethrough.

13. The guide of claim 12, wherein the sighting holes are round, and further comprising slotted sighting holes.

14. The guide of claim 13, wherein the slotted sighting holes allow placement of the sighting rod through the holes in an inclined position.

15. A method for positioning a distal femoral cutting guide into an angle which is perpendicular to a patient's mechanical axis, including the steps of:

(a) determining an angle that the patient's mechanical axis forms with respect to the patient's intramedullary canal;

(b) positioning an intramedullary alignment guide to a distal femur end of a patient's femur, wherein the alignment guide includes:

(1) a base including an attachment rod shaped to receive a distal femoral cutting guide, and (2) an angular adjustment means, pivotally secured to the base, wherein rotation of the angular adjustment means pivots the base about an axis which is coincident with the intramedullary canal of the patient, and wherein the adjustment means deflects the base into a selected angle with respect to the intramedullary canal of the patient;

(c) inserting an intramedullary rod through the alignment guide and into the patient's intramedullary canal;

(d) rotating the angular adjustment means to select an angle which is equal to the angle that the patient's mechanical axis forms with respect to the patient's intramedullary canal;

(e) placing the distal femoral cutting guide over the attachment rod; and (f) securing the cutting guide to the patient's femur.

16. The method of claim 15, further including the step of verifying that the distal femoral cutting guide is perpendicular with the patient's mechanical axis.

* * * * *